(12) United States Patent
Klaffenbach et al.

(10) Patent No.: US 9,895,056 B2
(45) Date of Patent: Feb. 20, 2018

(54) OPHTHALMIC MULTIPLE WAVELENGTH LASER ILLUMINATOR WITH A GRAPHICAL USER INTERFACE

(71) Applicant: Bausch & Lomb Incorporated, Rochester, NY (US)

(72) Inventors: David K. Klaffenbach, Imperial, MO (US); Brian McCary, Clayton, MO (US); John Goewert, St. Louis, MO (US); David H. Mordaunt, Los Gatos, CA (US)

(73) Assignee: Bausch & Lomb Incorporated, Rochester, NY (US)

( * ) Notice: Subject to any disclaimer, the term of this patent is extended or adjusted under 35 U.S.C. 154(b) by 538 days.

(21) Appl. No.: 14/072,859

(22) Filed: Nov. 6, 2013

(65) Prior Publication Data

US 2014/0128686 A1    May 8, 2014

Related U.S. Application Data

(60) Provisional application No. 61/723,086, filed on Nov. 6, 2012.

(51) Int. Cl.
*A61B 1/06* (2006.01)
*A61B 3/00* (2006.01)
*A61B 5/00* (2006.01)

(52) U.S. Cl.
CPC .......... *A61B 3/0008* (2013.01); *A61B 5/7435* (2013.01)

(58) Field of Classification Search
CPC ........ A61B 1/32; A61B 5/1459; A61B 5/1455
USPC .......................... 600/249; 606/3–5; 607/89
See application file for complete search history.

(56) References Cited

U.S. PATENT DOCUMENTS

| 2005/0234441 | A1 | 10/2005 | Bisch et al. .................... 606/38 |
| 2008/0287758 | A1* | 11/2008 | Benaron et al. ............... 600/339 |
| 2010/0110368 | A1 | 5/2010 | Chaum ......................... 351/158 |
| 2012/0218172 | A1* | 8/2012 | Border et al. ..................... 345/8 |
| 2012/0249376 | A1* | 10/2012 | Wen et al. ............. 343/700 MS |
| 2014/0058198 | A1* | 2/2014 | St. George et al. .......... 600/109 |
| 2014/0107428 | A1* | 4/2014 | LaConte ....................... 600/249 |

OTHER PUBLICATIONS

International Preliminary Report on Patentability for corresponding PCT Application No. PCT/US2013/68618 dated Apr. 7, 2014 pp. 12.

* cited by examiner

*Primary Examiner* — Jacqueline Johanas
*Assistant Examiner* — Tessa Matthews
(74) *Attorney, Agent, or Firm* — Michael L. Smith

(57) ABSTRACT

An ophthalmic laser illuminator 10 includes multiple laser devices 12-16. There are at least three different wavelengths of light emitted by the multiple laser devices 12-16 and each wavelength of light emitted by each laser device is outside of wavelengths blocked by a safety filter used for surgical treatment lasers 52. A controller 18 controls the multiple laser devices 12-16. A graphical user interface 32 is operably attached to the controller 18 for allowing a user to select a plurality of light parameters for a light beam exiting the illuminator 10.

20 Claims, 3 Drawing Sheets

OPHTHALMIC MULTIPLE WAVELENGTH LASER ILLUMINATOR WITH A GRAPHICAL USER INTERFACE

CROSS-REFERENCE TO RELATED APPLICATIONS

This application claims priority to U.S. Provisional Patent Application Ser. No. 61/723,086, filed 6 Nov. 2012. The entire disclosure of the above-referenced application is incorporated herein.

FIELD

The present disclosure relates to an ophthalmic illuminator using multiple wavelength lasers having a graphical user interface to control the color of the light exiting the illuminator.

BACKGROUND

This section provides background information related to the present disclosure which is not necessarily prior art.

The use of multiple wavelengths of laser light to produce a desired color of output light is known. The use of lasers for illumination is attractive for a variety of reasons. They produce significantly less heat than traditional incandescent light sources, they allow an illuminator to emit significantly more lumens of light than is typical in an ophthalmic illuminator, and their power/intensity level are easily and precisely controllable.

One problem with such a multiple wavelength laser illuminator, or with any illuminator, is the simultaneous use of a treatment laser. The problem arises because along with the treatment laser, there is required the use of a filter eliminating the bandwidth of the treatment laser from the view of the surgeon, to prevent damage to the surgeon's eye. Filtering out this narrow bandwidth of light corresponding to the treatment laser then affects the perceived color of light that is illuminating the tissue being treated because any part of the illuminating light bandwidth corresponding to the treatment laser wavelength will also be blocked by the safety filter of the surgeon's head set or the microscope.

The surgeon often wants to change the illuminating light color to better visualize tissue or to help distinguish one tissue type from another. Traditionally, a white illumination light is filter by physically placing different filter discs in the light path to eliminate certain bandwidths to produce a desired color or tint of light. This requires a complicated and expensive mechanical system that inserts and removes filters from the light path.

Therefore, it is desirable to have an illuminator that can produce a variety of light wavelengths to produce a desired color in an easy, accurate fashion without the need for a mechanical filter system and that will also compensate for the light wavelengths blocked by the treatment laser safety filter.

DRAWINGS

The drawings described herein are for illustrative purposes only of selected embodiments and not all possible implementations, and are not intended to limit the scope of the present disclosure.

Corresponding reference numerals indicate corresponding parts throughout the several views of the drawings.

DETAILED DESCRIPTION

Example embodiments will now be described more fully with reference to the accompanying drawings.

Figure 1:
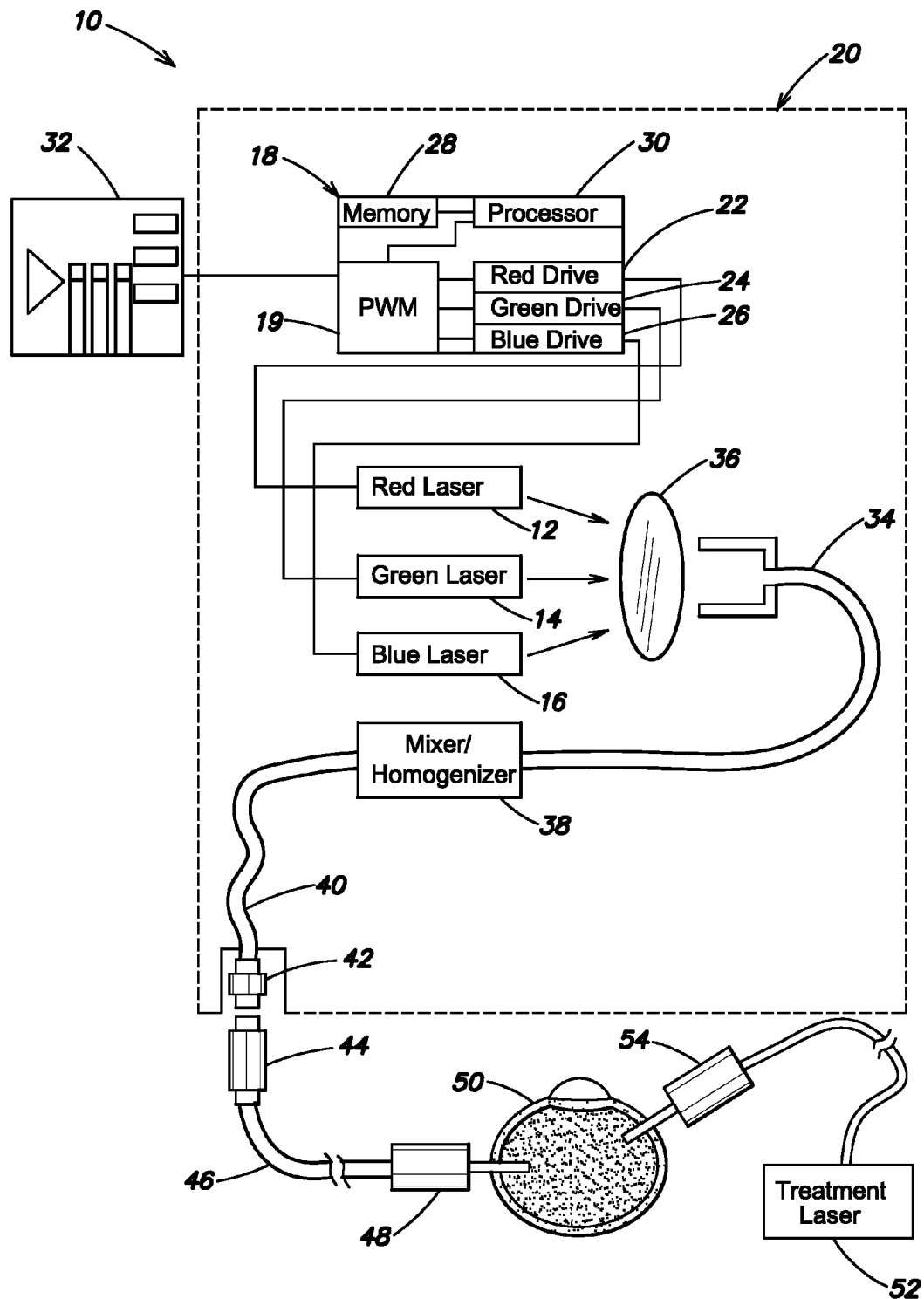
FIG. 1 is a block diagram of an illuminator, according to the present disclosure.

FIG. 1 shows an ophthalmic laser illuminator 10. The illuminator 10 includes multiple laser devices 12, 14, and 16. Each laser device 12-16 produces a different wavelength of light. There should be at least three different wavelengths of light emitted by the multiple laser devices 12-16, and each wavelength of light emitted by each laser device 12-16 is outside of wavelengths blocked by a safety filter used for surgical treatment lasers. The significance of the blocked wavelengths is discussed in detail below.

The laser illuminator 10 includes a controller 18 for controlling the multiple laser devices 12-16, and is part of an illuminator system defined by dashed line 20. The controller 18 includes a pulse width modulation (PWM) generator circuit 19 that provides input signals to multiple drive circuits 22, 24, and 26 corresponding to each laser device 12-16. The controller also includes a memory 28 for storing color data, including simulated illumination colors, favorite wavelengths of a surgeon, and other information. A processor 30 controls the PWM 19 based on input received from a graphical user interface (GUI) 32. The GUI 32 may be a touchscreen or other display, such as a computer screen and mouse, allowing a user to manipulate the wavelengths of light produced by the laser devices 12-16.

The example illuminator 10 shows three laser devices 12-16, but could include more than three laser devices. Also, the laser devices shown are red, green, and blue, but could include other colors or multiple devices of one or more colors, depending on the desired light output of the illuminator 10. For instance, the illuminator 10 could include red, cyan, and green laser devices, or 2 red, a blue, a cyan, and 2 green laser devices, or a red, a cyan, a blue, and a green laser device.

The light from each laser device 12-16 is directed to a patch fiber or other light guide 34 via focus lens 36. Mixer/Homogenizer 38 mixes the different wavelengths of light to eliminate color rings in light emitted from the illuminator system 20. Another patch fiber or light guide 40 transmits the mixed light beam to an output connector 42. The patch fiber 40 preferably has some manner of light scattering to help reduce speckle commonly observed in laser light. The manner in which speckle is reduced may be any suitable structure such as is known in the art.

The output connector 42 mates with a light fiber connector 44 attached to a length of fiber 46 that is attached to an illumination handpiece 48 for insertion into an eye 50. FIG. 1 also shows a treatment laser 52 connected to a laser treatment handpiece 54 that is inserted into the eye 50.

Figure 2:
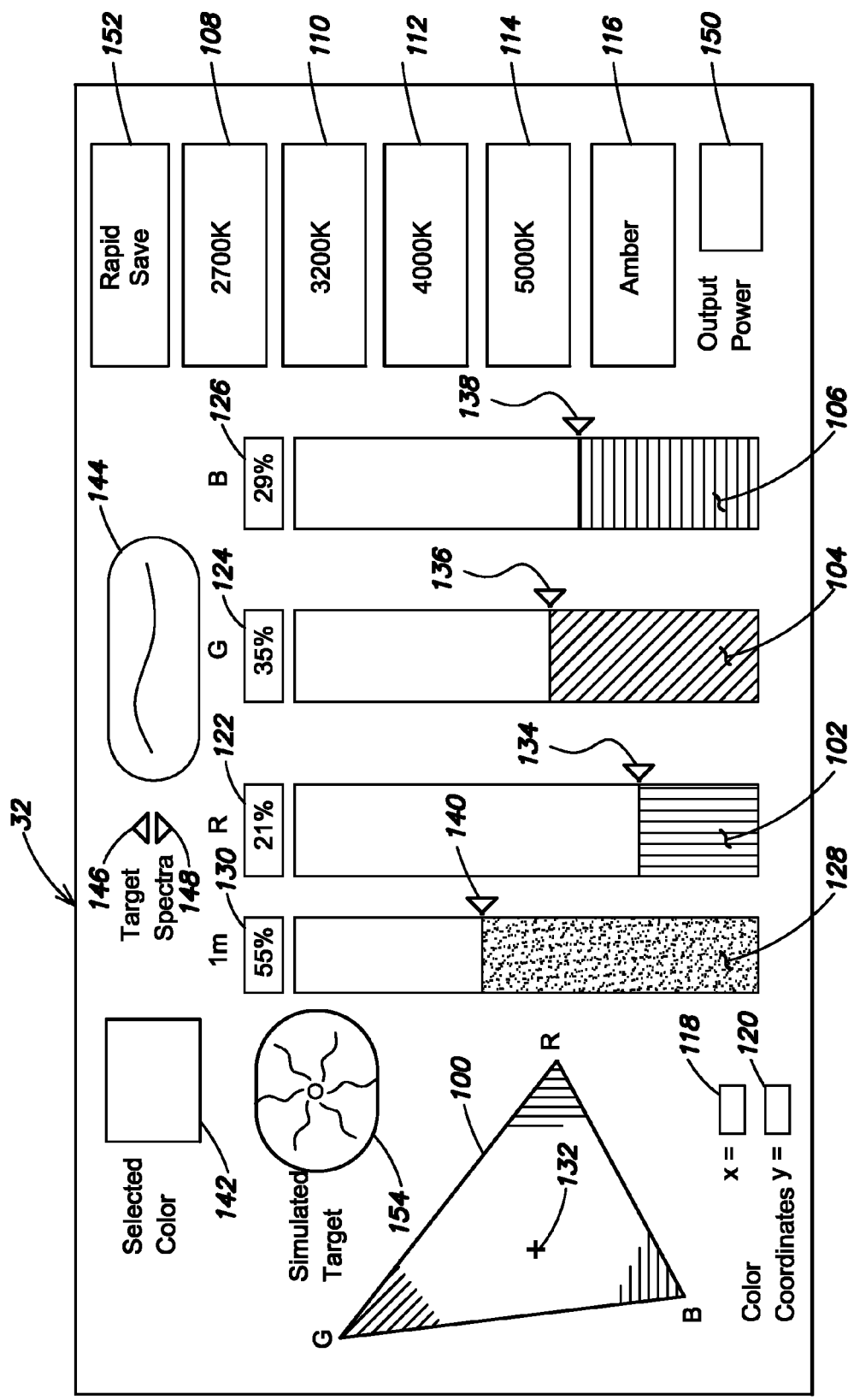
FIG. 2 is an example of a graphical user interface, according to the present disclosure.

The graphical user interface 32 is operably attached to the controller 18 for allowing a user to select a plurality of light parameters for a light beam exiting the illuminator 10. The GUI 32 is shown in detail in FIG. 2.

The GUI 32 allows a color of the light beam exiting the illuminator 10 at connector 42 to be set via multiple color-entry mechanisms. The color-entry mechanisms include a use of a chromaticity graph 100, slider bars 102, 104, and 106 for each different wavelength of light emitted by the laser devices 12-16, a plurality of color preset buttons 108, 110, 112, 114, and 116, a numeric entry of a color coordinate of the color desired at 118 and 120, and a numeric entry of a proportion of each wavelength comprising the light beam exiting the illuminator at 122, 124, and 126.

The GUI 32 allows a luminous flux level of the light beam exiting the illuminator to be set via multiple flux-entry mechanisms, including a master slider bar 128 and a numeric entry of a luminous flux value at 130.

After the GUI 32 is used to set the color and luminous flux level of the light beam exiting the illuminator via one of the multiple color-entry mechanisms and one of the multiple flux-entry mechanisms, the GUI 32 automatically updates all of the multiple color-entry mechanisms and the multiple flux-entry mechanisms to reflect the set color and luminous flux level. That is when one mechanism is used to set the wavelengths of the light beam exiting the illuminator 10 the other mechanisms on the GUI are automatically updated to reflect the wavelengths set by the user. For example, if a user uses a touchscreen to move selection cursor 132 of graph 100 to a desired color, the slider bars 102-106, and the coordinates at 118 and 120, and the proportion of each wavelength at 122-126 are updated to reflect and correspond to the change in the cursor 132 position.

The slider bars 122-126 may be used to individually change the proportion that each laser device contributes to the exiting light beam by moving the arrows 134, 136, and 138. Similarly, the luminous flux level may be changed by moving arrow 140.

In addition, the selected color of light exiting the illuminator can be simulated and displayed on the GUI 32 at 142. The area 142 of GUI 32 may simulate the color and the intensity of the light beam exiting the illuminator 10.

The multiple color-entry mechanisms also may include a selection of one of a plurality of spectral reflectance curves at 144. The spectral reflectance curves may be stored in memory 28 of the controller 18. The spectral reflectance curves may be selected by toggling through the stored curves using buttons 146, 148. The multiple color-entry mechanisms also include an entry of at least one spectral reflectance curve into the memory 28.

The GUI 32 may also include a display of an output power as a function of the set color and luminous flux level at 150. The displayed output power may be an aphakically-weighted power.

The GUI 32 may also include a save button 152 for saving the set color and luminous flux level for future use.

The GUI 32 may also include a display of a simulated target appearance at 154 based on data stored in a memory 28 of the controller 18 corresponding to the plurality of light parameters selected. The display at 154 represents the different tissue reflectances of the selected wavelengths and highlights the contrast between tissue types. For instance, blood vessels in the retina may reflect certain wavelengths differently from other tissue. The display at 154 can be used to assist in choosing the proper mix of wavelengths to enhance visualization of the target area.

The above GUI light parameter setting mechanisms are only examples. Other light setting mechanisms may be used, such as a pop-up numeric key pad to directly enter a color coordinate, luminous flux value, or proportion of each wavelength component.

The following are examples of the wavelengths of light emitted by the laser devices 12-16 that may be compatible with a treatment laser's safety filter.

The wavelengths of light may include a red light with a dominant wavelength of at least 620 nanometers (nm), a blue light with a dominant wavelength of less than 480 nm, and a green light with a dominant wavelength between 552 and 557 nm.

The three wavelengths of light emitted by the laser devices may include a red light with a dominant wavelength of at least 620 nm, a blue light with a dominant wavelength of less than 480 nm, and a cyan light with a dominant wavelength between 500 and 512 nm.

If there are at least four different wavelengths of light emitted by the multiple laser devices they may include a red light with a dominant wavelength of at least 620 nm, a blue light with a dominant wavelength of less than 480 nm, a cyan light with a dominant wavelength between 500 and 512 nm, and a green light with a dominant wavelength between 552 and 557 nm.

If there are at least four different wavelengths of light emitted by the multiple laser devices they may include a red light with a dominant wavelength of at least 620 nm, a blue light with a dominant wavelength of less than 480 nm, a cyan light with a dominant wavelength between 500 and 512 nm, and a green light with a dominant wavelength between 552 and 570 nm.

It is also possible to produce a constant color illumination even if one of the laser devices falls within the bandwidth blocked by a treatment safety filter, if there are at least four different wavelengths of light emitted by the multiple laser devices and at least three different wavelengths of light are sufficiently outside of the wavelengths blocked by the safety filter. For instance, with a 532 nm treatment laser a system could have illumination laser devices with wavelengths of 465 nm, 490 nm, 532 nm, and 636 nm. Obviously, the 532 nm illumination laser device would be blocked by the safety filter, but the other three laser devices could still produce a wide range of colors that would not be compromised by the safety filter.

The at least three wavelengths of light emitted by the laser devices 12-16 may include a red light with a dominant wavelength of at least 620 nm, a blue light with a dominant wavelength of less than 480 nm, and a green light with a dominant wavelength between 552 and 570 nm.

Figure 3:
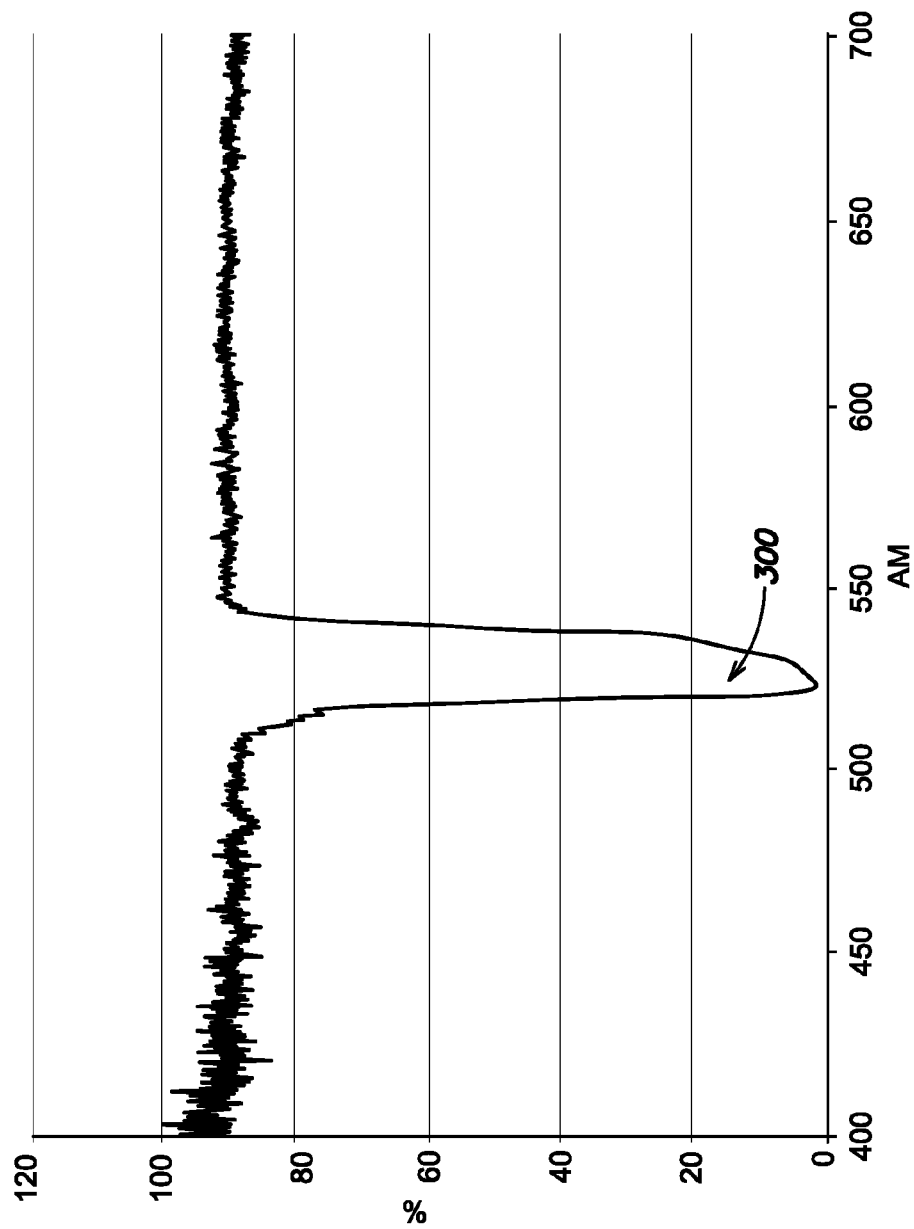
FIG. 3 is an example of a safety notch filter.

The at least three wavelengths of light emitted by the multiple laser devices for ophthalmic illumination typically should not include light wavelengths between 512 nm and 552 nm. This is because the typical treatment laser has a nominal wavelength of 532 nm. Ophthalmic surgical microscopes are equipped with laser safety notch filters to highly attenuate laser light which would otherwise be reflected into the surgeon's eye. These filters must highly attenuate the expected wavelength of the laser (e.g. 532 nm or 577 nm) but due to tolerances in the laser wavelength and tolerances of the filters, typically have a notch width of about 30 nm. The transmission curve of a typical filter for a 532 nm system is shown at FIG. 3. As can be seen, the notch 300 is centered about 532 nm and is more or less 30 nm wide. The example filter attenuates significantly from about 512 nm to about 540 nm. For illumination system 20 to be unaffected by such a filter, or by similarly broad filters with a different center wavelength, one would avoid using spectrum in 40 nm bands around the lasers wavelengths, specifically 512 to 552 nm (for a 532 nm treatment laser), and 557 to 597 nm (for a 577 nm treatment laser).

The at least three wavelengths of light emitted by the multiple laser devices 12-16 should not include light wavelengths between 557 nm and 597 nm for a 577 nm treatment laser.

By providing laser devices that produce wavelengths sufficiently away from the nominal wavelength of the treatment lasers to be used with the illuminator 10, a constant color light beam exiting the illuminator 10 can be produced that is not influenced by the safety filter of a microscope or head-set used by the surgeon.

As can be seen from the above discussion, if a safety filter with a different nominal blocking region is used, then the acceptable wavelengths of illuminating laser devices may be different.

It is also noted that a white LED comprised of a blue LED and phosphor with yellow output predominantly above 552 nm could be used as a light source compatible with 532 nm safety filter.

A broadband light source, such as xenon short-arc, pre-filtered to remove a band matching that of the safety filter would also provide light of unchanging color with regard to use of the laser safety filter.

The above illuminator designs are intended to work with a large set of safety filters. The spectral content of the light can be chosen with few limitations for use with a specific design of safety filter.

It is presumed that the quantity of the three or four individual wavelength laser sources will be chosen to provide the desired colors and brightness otherwise required for a given application.

The illuminator 10 may be incorporated into a surgical console, such as the Stellaris PC™ available from Bausch & Lomb Incorporated or illuminator 10 may be a stand-alone system that cooperates with such a surgical console and a treatment laser. Similarly, the treatment laser may be part of the surgical console or may be a stand-alone system. If the illuminator 10 is incorporated into a surgical console, GUI 32 will typically be the display screen of the console.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

We claim:

1. An ophthalmic laser illuminator comprising:
multiple laser devices, wherein there are at least three different wavelengths of light emitted by the multiple laser devices and each wavelength of light emitted by each laser device is outside of wavelengths blocked by a safety filter used for surgical treatment lasers;
a controller for controlling the multiple laser devices;
a graphical user interface operably attached to the controller for allowing a user to select a plurality of light parameters for a light beam exiting the illuminator;
wherein the graphical user interface allows a color of the light beam exiting the illuminator to be set via multiple color-entry mechanisms including at least a use of a chromaticity graph, a slider bar for each different wavelength of light emitted by the laser devices, a plurality of color preset buttons, a numeric entry of a color coordinate of the color desired, and a numeric entry of a proportion of each wavelength comprising the light beam exiting the illuminator;
wherein the graphical user interface allows a luminous flux level of the light beam exiting the illuminator to be set via multiple flux-entry mechanisms including at least a master slider bar and a numeric entry of a luminous flux value; and
wherein, after the graphical user interface is used to set the color and luminous flux level of the light beam exiting the illuminator via one of the multiple color-entry mechanisms and one of the multiple flux-entry mechanisms, the graphical user interface automatically updates all of the multiple color-entry mechanisms and the multiple flux-entry mechanisms to reflect the set color and luminous flux level.

2. The illuminator of claim 1 wherein the at least three wavelengths of light emitted by the laser devices include a red light with a dominant wavelength of at least 620 nm, a blue light with a dominant wavelength of less than 480 nm, and a green light with a dominant wavelength between 552 and 557 nm.

3. The illuminator of claim 1 wherein the at least three wavelengths of light emitted by the laser devices include a red light with a dominant wavelength of at least 620 nm, a blue light with a dominant wavelength of less than 480 nm, and a cyan light with a dominant wavelength between 500 and 512 nm.

4. The illuminator of claim 1 wherein there are at least four different wavelengths of light emitted by the multiple laser devices and include a red light with a dominant wavelength of at least 620 nm, a blue light with a dominant wavelength of less than 480 nm, a cyan light with a dominant wavelength between 500 and 512 nm, and a green light with a dominant wavelength between 552 and 557 nm.

5. The illuminator of claim 1 wherein there are at least four different wavelengths of light emitted by the multiple laser devices and include a red light with a dominant wavelength of at least 620 nm, a blue light with a dominant wavelength of less than 480 nm, a cyan light with a dominant wavelength between 500 and 512 nm, and a green light with a dominant wavelength between 552 and 570 nm.

6. The illuminator of claim 1 wherein the at least three wavelengths of light emitted by the laser devices include a red light with a dominant wavelength of at least 620 nm, a blue light with a dominant wavelength of less than 480 nm, and a green light with a dominant wavelength between 552 and 570 nm.

7. The illuminator of claim 1 wherein the at least three wavelengths of light emitted by the multiple laser devices do not include light wavelengths between 512 nm and 552 nm.

8. The illuminator of claim 1 wherein the at least three wavelengths of light emitted by the multiple laser devices do not include light wavelengths between 557 nm and 597 nm.

9. The illuminator of claim 1 wherein there are at least four different wavelengths of light emitted by the multiple laser devices and at least three of the four different wavelengths of light are outside of the wavelengths blocked by the safety filter.

10. The illuminator of claim 1 wherein the graphical user interface includes a touch-screen display.

11. The illuminator of claim 1 further including a light mixer for combining each wavelength of light emitted by each laser device into the light beam exiting the illuminator.

12. The illuminator of claim 11 further including a homogenizer for minimizing perceived color rings in the light beam exiting the illuminator.

13. The illuminator of claim 1 wherein the multiple color-entry mechanisms further include a selection of one of a plurality of spectral reflectance curves stored in a memory of the controller.

14. The illuminator of claim 1 wherein the multiple color-entry mechanisms further include an entry of at least one spectral reflectance curve.

15. The illuminator of claim 1 wherein the graphical user interface further includes a display of a simulated color and intensity of the light beam exiting the illuminator.

16. The illuminator of claim 1 wherein the graphical user interface further includes a display of an output power as a function of the set color and luminous flux level.

17. The illuminator of claim 16 wherein the displayed output power is an aphakically-weighted power.

18. The illuminator of claim 1 further including a save button for saving the set color and luminous flux level for future use.

19. The illuminator of claim 1 wherein the graphical user interface further includes a display of a simulated target appearance based on data stored in a memory of the controller corresponding to the plurality of light parameters selected.

20. An ophthalmic laser illuminator comprising:
multiple laser devices, wherein there are at least three different wavelengths of light emitted by the multiple laser devices and each wavelength of light emitted by each laser device is outside of wavelengths blocked by a safety filter used for surgical treatment lasers;
a controller for controlling the multiple laser devices;
a graphical user interface operably attached to the controller for allowing a user to select a plurality of light parameters for a light beam exiting the illuminator; and
wherein the graphical user interface displays a simulated target appearance based on data stored in a memory of the controller corresponding to the plurality of light parameters selected.

* * * * *